United States Patent [19]
Brown et al.

[11] Patent Number: 5,379,917
[45] Date of Patent: Jan. 10, 1995

[54] DUAL SOAP AND FRAGRANCE DISPENSER

[75] Inventors: Douglas S. Brown; David F. Scherger, both of Toledo; George C. Heilman, Northwood; Robert B. Brown, Toledo, all of Ohio

[73] Assignee: Fresh Products, Inc., Toledo, Ohio

[21] Appl. No.: 24,448

[22] Filed: Mar. 1, 1993

[51] Int. Cl.⁶ .............................................. B67D 5/00
[52] U.S. Cl. ...................................... 222/4; 222/105; 222/135; 222/181; 222/325; 261/26; 261/30; 261/DIG. 65
[58] Field of Search ................... 222/4, 105, 135, 180, 222/181, 325, 642, 129; 261/26, 30, DIG. 65

[56] References Cited

U.S. PATENT DOCUMENTS

| | | | |
|---|---|---|---|
| Re. 33,864 | 3/1992 | Steiner et al. | 261/30 |
| 2,925,202 | 2/1960 | Stevens | 222/190 |
| 3,522,935 | 8/1970 | Lewis | 239/60 X |
| 3,993,444 | 11/1976 | Brown et al. | 239/60 X |
| 4,154,375 | 5/1979 | Bippus | 222/325 |
| 4,294,778 | 10/1981 | DeLuca | 239/38 X |
| 4,570,827 | 2/1986 | Roggenburg, Jr. et al. | 222/181 X |
| 4,741,461 | 5/1988 | Williamson et al. | 222/325 X |
| 4,743,406 | 5/1988 | Steiner et al. | 261/30 |
| 4,881,652 | 11/1989 | Schiemann | 222/129 X |
| 4,903,584 | 2/1990 | Styles | 239/60 X |
| 4,921,131 | 5/1990 | Binderbauer et al. | 222/181 X |
| 4,946,070 | 8/1990 | Albert et al. | 222/52 |
| 4,946,072 | 8/1990 | Albert et al. | 222/181 X |
| 4,967,935 | 11/1990 | Celest | 222/63 |
| 5,147,582 | 9/1992 | Holzner, Sr. et al. | 239/60 X |

FOREIGN PATENT DOCUMENTS 461572  5/1928  Germany ........................ 222/129

*Primary Examiner*—Andres Kashnikow
*Assistant Examiner*—Joseph A. Kaufman
*Attorney, Agent, or Firm*—Knobbe, Martens, Olson & Bear

[57] ABSTRACT

A dual dispenser dispenses both soap and fragrance for washrooms. The dispenser has a mounting plate for mounting on a surface in the washroom and has a lower support for a box containing a flexible bag of soap with the bag having a flexible tube extending out of the box. A container with a fragrance source is mounted in the top of the box and a fan is located thereabove which is driven by a small motor mounted on an upper support of the mounting plate. A battery is also located on the box adjacent the fragrance container. Switch contacts are in circuit with the motor and the battery for operating the motor and fan when the switch contacts are closed. A cover for the mounting plate has a hand-operated actuating plate which squeezes the tube to dispense soap and closes the contacts to operate the fan when the actuating plate is pushed, thus dispensing both soap and fragrance in a single motion.

39 Claims, 2 Drawing Sheets

DUAL SOAP AND FRAGRANCE DISPENSER

FIELD OF THE INVENTION

This invention relates to a dual dispenser for dispensing both soap and fragrance.

BACKGROUND OF THE INVENTION

Soap dispensers are commonly used in public washrooms. They are located near the wash basin and have actuating plates for dispensing soap into the hand of a person when the plate is pushed or pulled.

Fragrance dispensers are also often used in public washrooms. The fragrance is usually dispensed continuously or activated when a light in the washroom is turned on and the unit is located high on the washroom wall. Of course, both the soap dispenser and the fragrance dispenser require separate maintenance. Yet due to the fragrance dispenser's awkward location, frequently, when the fragrance source is used up, it is not replaced on a regular basis.

SUMMARY OF THE INVENTION

The present invention provides a dispenser which dispenses both soap and fragrance simultaneously. The dual dispenser is also designed so that the fragrance and the soap each last the same amount of time. The dual dispenser has a mounting plate for mounting the dispenser on a surface in the washroom. The mounting plate has a lower support which supports a box containing a flexible bag of soap. The bag has a flexible tube extending out of the box and downwardly toward the bottom of the dispenser, which is open. A container with the fragrance source is located above and preferably directly on the top of the box containing the soap. The mounting plate also has an upper support on which a motor and fan are mounted. The motor and fan are located directly above the fragrance source for dispensing the fragrance when the fan is driven.

The soap, fragrance source, and a battery are housed in the box. When the box is placed in the dispenser, the electrical circuit is completed. The action of dispensing soap also activates the motor and fan which, in turn, dispenses fragrance in the area.

The dispenser further has a cover for the mounting plate with openings therein through which the fragrance can be dispensed. A hand-operated actuating plate is movably carried by the cover and is effective to squeeze the tube to dispense soap and at the same time close the switch contacts to operate the fan when the actuating plate is moved by a person. A time delay is part of the circuit so that when contact is made, the operation of the fan and motor can be extended for a longer period of time than when the actuating plate is moved.

In a preferred form, the soap box, the contained fragrance source, and the battery are supplied as a single unit. The fragrance source can be located on top of the box and the box has a recess which contains the battery. The mounting plate has electrical contacts and the circuit is completed when the box (soap, fragrance source, and battery) is placed in the dispenser. When the soap in the bag is used up, the entire unit is removed and replaced with a new one containing a full bag of soap, a new fragrance source and a fresh battery. Thus, maintenance is substantially reduced by combining the soap and fragrance systems and costs are reduced since the dispenser housing is dual purpose. The fragrance source is designed to be exhausted when the soap supply is depleted.

It is, therefore, a principal object of the invention to provide a dual dispenser for dispensing both soap and fragrance.

Another object of the invention is to provide a dual dispenser for soap and fragrance which are both dispensed when an actuating plate on the dispenser is moved.

Yet a further object of the invention is to provide a box having a bag of soap, a container having a supply of fragrance, and a recess with a battery all supplied as one unit.

BRIEF DESCRIPTION OF THE DRAWINGS

Many other objects and advantages of the invention will be apparent from the following detailed description of a preferred embodiment thereof, reference being made to the accompanying drawings, in which.

DETAILED DESCRIPTION OF THE PREFERRED EMBODIMENT

Figure 1:
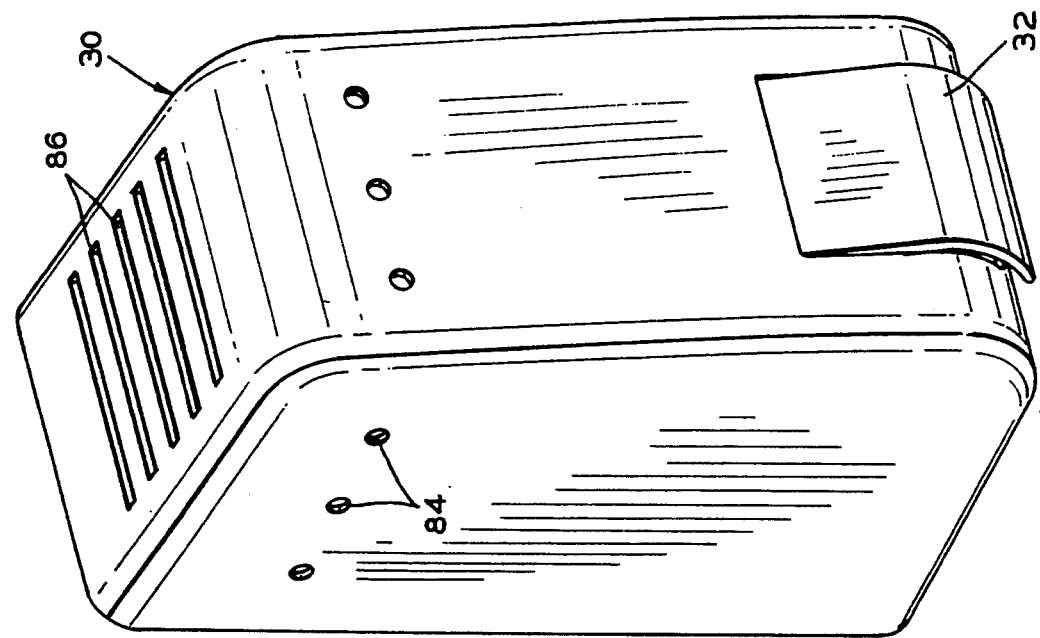
FIG. 1 is a somewhat schematic, exploded view in perspective of a dual dispenser in accordance with the invention.
Figure 1:
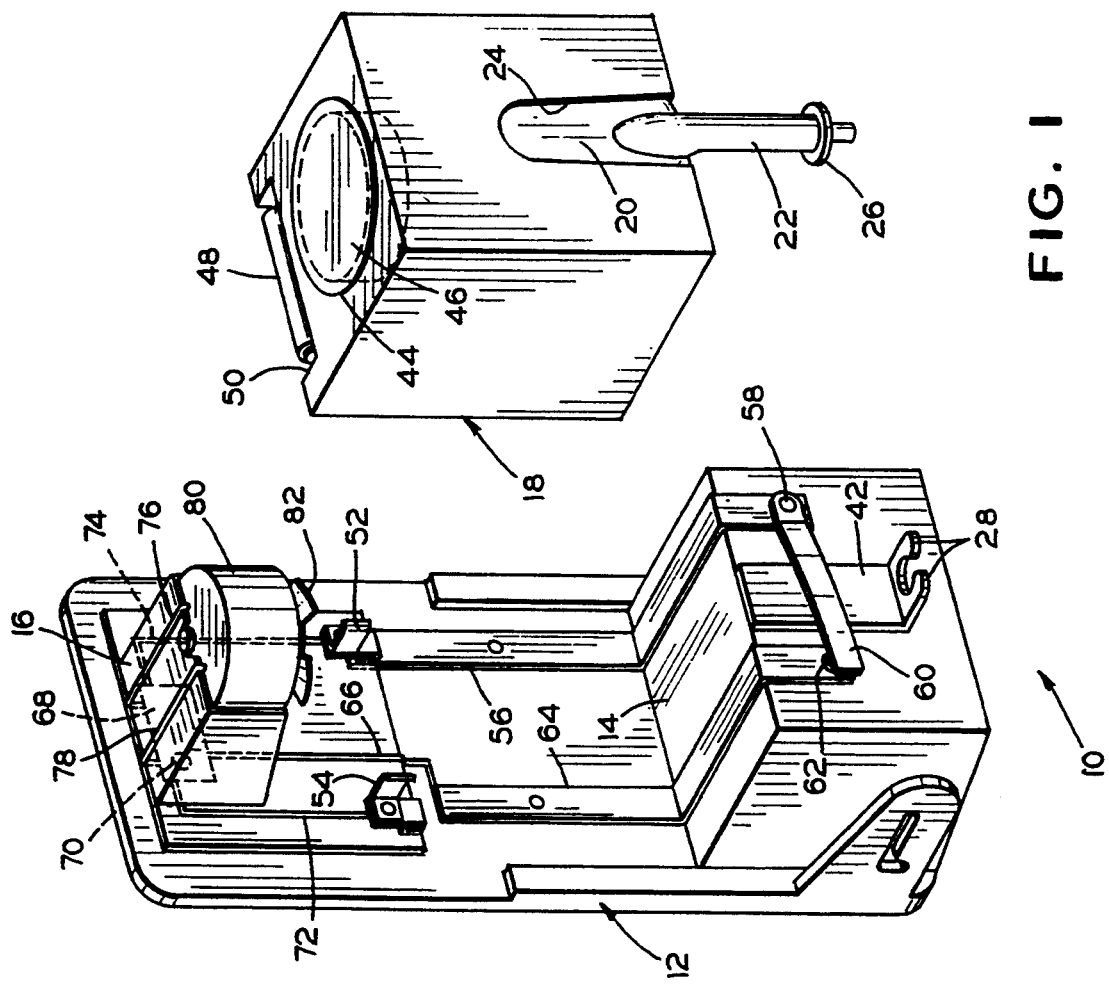

Referring to the drawings, a dual dispenser according to the invention is indicated at 10. It includes a mounting plate 12 which is suitably affixed to a wall or other surface of a washroom. The plate 12 has a lower shelf or support 14 and an upper support 16. A box 18 contains a flexible bag 20 of thick liquid soap with a flexible dispensing tube 22 extending through an opening 24 in the box 18 with a flanged spout 26. The box 18 is originally fully enclosed when purchased but a perforate section is removed to leave the opening 24 and the tube 22 is pulled out from the opening prior to placing the box 18 on the shelf 14 of the mounting plate 12. The flanged spout is then inserted between clips 28 at the bottom of the mounting plate 12 when the box 18 is placed on the shelf 14.

Figure 2:
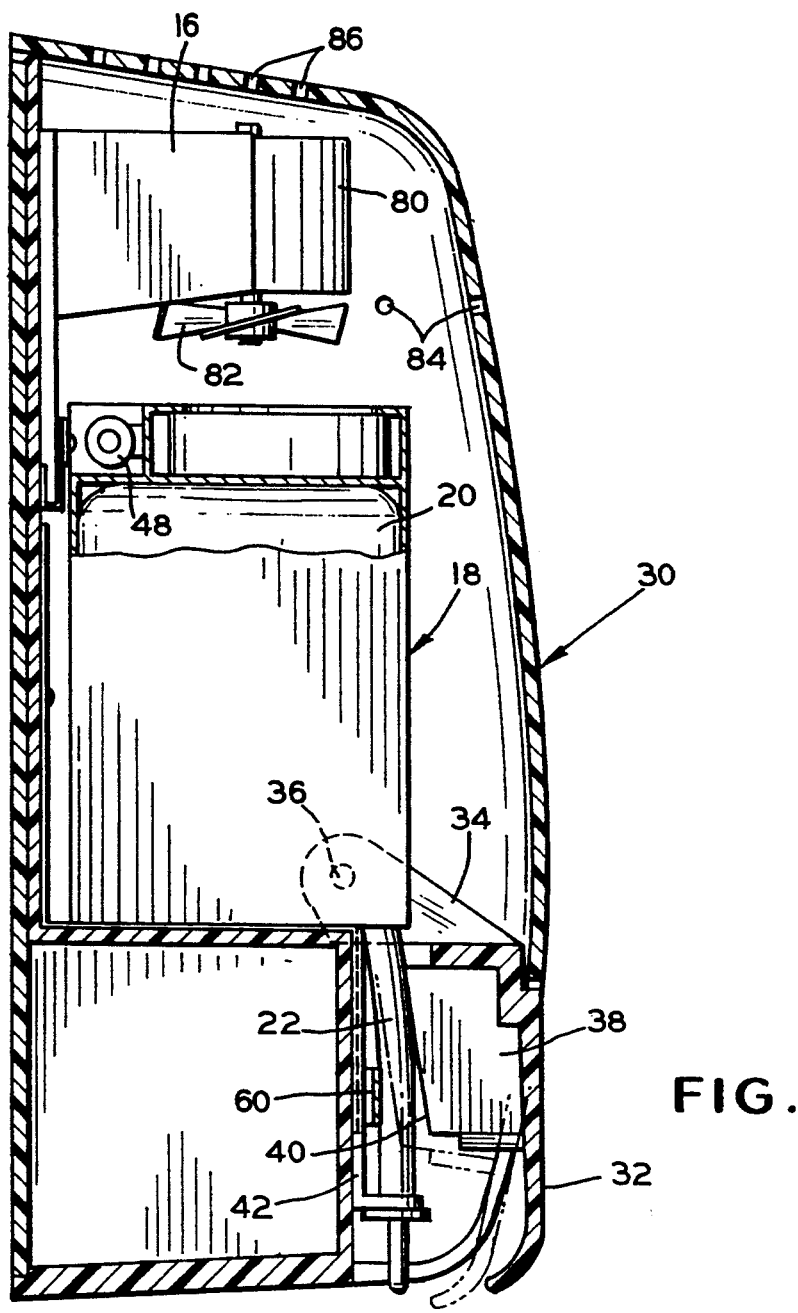
FIG. 2 is a somewhat schematic view in longitudinal cross section of the dual dispenser.

A cover 30 for the dispenser 10 has an actuating plate 32 (FIG. 2) near the bottom with the plate having ears 34 which are pivotally mounted on a rod 36. A squeeze bar 38 is affixed to the actuating plate and has a slanted surface 40 Which squeezes the tube 22 against a front surface 42 of the mounting plate 12 when the actuating plate 32 is moved.

In accordance with the invention, the box 18 of soap has a container 44 located thereabove containing a source of fragrance such as gel 46 and a battery 48. The box 18 has a recess 50 with the battery 48 affixed therein. The recess 50 is longer than the battery 48 so that electrical contacts 52 and 54 on the mounting plate 12 can electrically engage the ends of the battery 48 when the box 18 and the container 44 are placed on the shelf 14. The fragrance gel has a top which is removed before the box and container are put in place.

The electrical contact 52 is electrically connected with a conducting strip 56 which extends downwardly to a fastener 58 on the front surface 42 of the mounting plate 12. The fastener 58 electrically connects the conducting strip 56 with a switch blade or strip 60. The switch blade 60 is located behind the flexible tube 22 when the box 18 is in place and makes electrical contact with a contact 62 when the actuating plate 32 is moved to squeeze the flexible tube 22. The electrical contact 62 is connected to a conducting strip 64 which extends upwardly near the contact 54 and has a conductor 66 connected with a PC board 68 having a timer 70 which is preferably solid state. A conductor 72 also electrically connects the contact 54 with the PC board. Finally, a conductor 74 connects the PC board with the electrical contact 52.

Conductors 76 and 78 also extend from the PC board 68 to a small, commercially-available electric motor 80 which drives a fan 82 located below the motor. The motor 80 is mounted on the upper support 16 of the mounting plate 12. When the fan 82 rotates, it dispenses fragrance through openings 84 and slits 86 in the cover 30.

Figure 3:
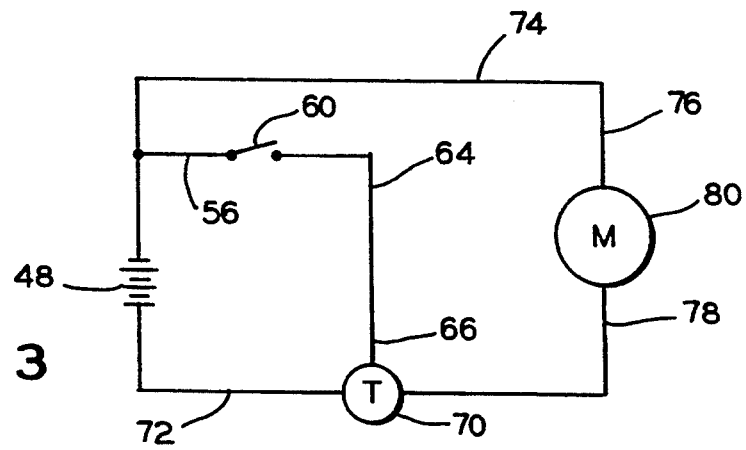
FIG. 3 is a diagram of a circuit used in the dispenser.

Referring to FIG. 3, when the switch blade 60 is closed, it completes a circuit from the battery 48 to the timer 70 which then conducts for a predetermined period of time such as fifteen to twenty seconds. A circuit is then completed through the timer 70, the battery 48, and the motor 80, until the timer opens. The timer can also be a chip which is programmed to operate the fan for a given period of time periodically. The fan could also be run continuously for use in high odor areas. The dispenser can also have an LED which is turned on when the fan is running. In place of the fan, a heat-activated material could be used to melt a plastic bar that is impregnated with fragrance. This would be accomplished either through a battery or by plugging into an electrical outlet. The dispenser could also be used with a light-sensitive eye to turn the fan on when the washroom lights are on.

In place of building the fragrance container into the top of the soap box, a separate plastic shroud could be employed which fits over the top of a standard box with the shroud housing both the battery and the fragrance source. A dispenser with a fragrance source could also be used with a reservoir type of soap dispenser rather than a separate soap box.

Various modifications of the above-described embodiments of the invention will be apparent to those skilled in the art, and it is to be understood that such modifications can be made without departing from the scope of the invention, if they are within the spirit and the tenor of the accompanying claims.

We claim:

1. A dual dispenser for soap and fragrance comprising a mounting plate for mounting the dispenser on a surface in a washroom, said mounting plate having a lower support and an upper support, a box containing a flexible bag of soap supported on said lower support, said bag having a flexible tube extending out of said box, a container of fragrance gel above said box, a motor mounted on said upper support, a fan driven by said motor, a battery, switch contacts in circuit with said motor and said battery, a cover for said mounting plate, and a hand-operated actuating plate carried by said dispenser, said actuating plate being effective to squeeze said tube to dispense soap and to close said contacts to operate said fan said actuating plate is moved.

2. A dual dispenser according to claim 1 wherein said fragrance container is mounted on an upper portion of said box as a unit.

3. A dual dispenser according to claim 2 wherein said battery is mounted on said box adjacent said fragrance container.

4. A dual dispenser according to claim 1 wherein a time delay component is mounted in circuit with said contacts and said battery whereby said circuit is completed for a period of time longer than said actuating plate is actuated.

5. A supply unit for a dual dispenser for soap and fragrance, said unit comprising a box containing a flexible bag of soap, a source of fragrance on a top of said box, and a battery mounted on the top of said box.

6. A supply unit according to claim 5 wherein said box is of generally rectangular parallelepiped configuration and said flexible bag of soap has a flexible tube communicating therewith.

7. A supply unit according to claim 5 wherein said box has a recess in which said battery is located.

8. A supply unit according to claim 7 wherein said recess has a length exceeding the length of the battery whereby said recess can receive contact means extending thereinto for making electrical contact with said battery.

9. A dual dispenser for soap and fragrance comprising a mounting plate for mounting the dispenser on a surface, said mounting plate having a support extending therefrom, a box containing a bag of soap supported on said support, said bag having a flexible tube extending out of said box, a container of fragrance-emitting material in said dispenser, a motor in said dispenser, a fan near said container and driven by said motor, a source of power for operating said motor, switch contacts in circuit with said motor and said power source, a cover for said dispenser, an actuating plate carried by said dispenser, said actuating plate being effective to squeeze said tube to dispense soap and to close said contacts to operate said fan when said actuating plate is moved.

10. A dual dispenser according to claim 9 wherein said mounting plate has an upper support, said motor being supported on said upper support, and said container of fragrance-emitting material being above said box.

11. A dual dispenser according to claim 9 wherein said power source is a battery.

12. A dual dispenser according to claim 9 wherein said fragrance container is mounted on an upper portion of said box as a unit.

13. A dual dispenser according to claim 12 wherein said battery is mounted on said box adjacent said fragrance container.

14. A dual dispenser according to claim 13 wherein said box has an upper recess in which said battery is located.

15. A dual dispenser according to claim 14 wherein said recess has a length exceeding the length of said battery whereby said recess can receive contact means on said mounting plate and extending into said recess for making electrical contact with said battery.

16. A dual dispenser for soap and fragrance comprising a mounting plate for mounting the dispenser on a surface in a washroom, a source of soap supported in said dispenser, a source of fragrance above said soap source, a motor mounted on said mounting plate, a fan driven by said motor, a battery, circuit means connecting said motor and said battery, a cover for said mounting plate, and hand-operated actuating means carried by said dispenser and effective to dispense soap when actuated manually.

17. A dual dispenser according to claim 16 wherein switch contacts are in said dispenser and closed when said actuating means is moved to connect said battery and said motor through said circuit means.

18. A dual dispenser according to claim 16 wherein said source of soap is a box containing a flexible bag of soap and said bag has a flexible tube extending out of said box and squeezed when said actuating means is actuated.

19. A supply unit for a dual dispenser for soap and fragrance, said unit comprising:
 a receptacle defining a cavity and a channel connected to the lower portion of said cavity through which soap is dispensed to the hands of the user;
 a supply of soap within said receptacle;
 a container connected to said receptacle defining an opening through which fragrance is dispensed through evaporation; and
 a source of fragrance within said container other than said supply of soap, said unit sized and shaped to be insertable into a dual dispenser for soap and fragrance.

20. The supply unit of claim 19, further comprising a top which forms a seal which prevents said source of frangrance from evaporating through said opening, wherein when said seal is released fragrance within said container evaporates through said opening.

21. The supply unit of claim 20, wherein said receptacle further comprises a spout.

22. The supply unit of claim 19, wherein said receptacle is larger than said container.

23. A supply unit for a dual dispenser for soap and fragrance, said unit comprising:
 a receptacle capable of securing a supply of soap to said unit;
 a container connected to said receptacle defining an opening through which fragrance is dispensed through evaporation;
 a source of fragrance within said container other than said supply of soap; and
 a power source connected to said unit, said unit sized and shaped to be insertable into a dual dispenser for soap and frangrance.

24. The supply unit of claim 23, further comprising a seal for said container which is opened to enable said supply unit to dispense fragrance.

25. The supply unit of claim 24, wherein said receptacle further comprises a spout.

26. The supply unit of claim 25, further comprising a supply of soap.

27. A supply unit for a dual dispenser for soap and fragrance, said unit comprising:
 a receptacle;
 a first container within said receptacle;
 a supply of soap within said first container;
 a second container within said receptacle defining an opening through which fragrance is dispensed through evaporation;
 a source of fragrance within said second container other than said supply of soap, said unit sized and shaped to be insertable into a dual dispenser for soap and fragrance; and
 a top which forms a seal which prevents frangrance from evaporating through said opening, wherein when said seal is removed fragrance within said container evaporates through said opening.

28. The supply unit of claim 27, wherein said first container further comprises a spout.

29. The supply unit of claim 27, wherein said first container is larger than said second container.

30. A dispenser, comprising:
 a housing defining a cavity sized and shaped to receive a supply of soap and a space sized and shaped to receive a source of fragrance, said housing defining an opening through which fragrance in said space is dispensed and a channel through which soap within said cavity is dispensed, said dispenser further comprising an actuator to dispense the soap from said dispenser.

31. The dispenser of claim 30, further comprising a mounting element for securing said dispenser to a surface.

32. The dispenser of claim 30, further comprising a mechanism to accelerate the dispensement of fragrance from a source of fragrance within said housing.

33. The dispenser of claim 32, wherein said mechanism comprises a fan.

34. The dispenser of claim 33, wherein said actuator activates said mechanism.

35. A dispenser, comprising:
 a housing defining a cavity sized and shaped to receive a supply of soap, said housing defining a space sized and shaped to receive a source of fragrance, said housing further defining an opening allowing a source of fragrance in said space to dispense fragrance through said opening and a channel through which a supply of soap within said cavity is dispensed;
 an actuator to dispense soap from said dispenser;
 a mechanism to accelerate the dispensement of fragrance through said opening from a source of fragrance within said housing, wherein said actuator activates said mechanism.

36. The dispenser of claim 35, wherein said mechanism is electrical.

37. The dispenser of claim 36, wherein said mechanism further comprises a normally open circuit arranged to cooperate with a power source, said circuit closable by said actuator.

38. A dispenser, comprising:
 a housing defining a cavity sized and shaped to receive a supply of soap, said housing defining a space sized and shaped to receive a source of fragrance;
 an actuator to dispense soap from said dispenser;
 a mechanism to accelerate the dispensement of fragrance from a source of fragrance within said housing, wherein said actuator activates said mechanism and said mechanism includes a fan.

39. The dispenser of claim 38, wherein said mechanism further comprises a motor and a circuit arranged to cooperate with a power source to drive said fan.

* * * * *